(12) United States Patent
Endo et al.

(10) Patent No.: US 10,548,483 B2
(45) Date of Patent: Feb. 4, 2020

(54) IMAGE PROCESSING APPARATUS AND IMAGE PROCESSING METHOD

(71) Applicant: CANON KABUSHIKI KAISHA, Tokyo (JP)

(72) Inventors: Takaaki Endo, Urayasu (JP); Itaru Otomaru, Kawasaki (JP); Kiyohide Satoh, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 203 days.

(21) Appl. No.: 15/854,250

(22) Filed: Dec. 26, 2017

(65) Prior Publication Data
US 2018/0192881 A1     Jul. 12, 2018

(30) Foreign Application Priority Data

Jan. 6, 2017 (JP) ................................. 2017-001263

(51) Int. Cl.
| | | |
|---|---|---|
| *A61B 5/00* | (2006.01) | |
| *A61B 8/08* | (2006.01) | |
| *G06K 9/62* | (2006.01) | |
| *G02B 21/36* | (2006.01) | |

(52) U.S. Cl.
CPC .......... *A61B 5/0095* (2013.01); *A61B 5/0091* (2013.01); *A61B 5/7203* (2013.01); *A61B 8/0825* (2013.01); *A61B 8/5269* (2013.01); *G02B 21/367* (2013.01); *G06K 9/6202* (2013.01)

(58) Field of Classification Search
CPC ... A61B 5/0095; A61B 5/0091; A61B 5/7203; A61B 8/0825; A61B 8/5269; A61B 8/085; A61B 2576/00; G06T 3/0068; G06T 1/0007; G06K 9/32; G06K 9/6202; G02B 21/367

See application file for complete search history.

(56) References Cited

U.S. PATENT DOCUMENTS

| | | |
|---|---|---|
| 6,792,370 B2 | 9/2004 | Satoh et al. |
| 6,993,450 B2 | 1/2006 | Takemoto et al. |
| 7,092,109 B2 | 8/2006 | Satoh et al. |
| 7,130,754 B2 | 10/2006 | Satoh et al. |
| 7,411,594 B2 | 8/2008 | Endo et al. |
| 7,446,768 B2 | 11/2008 | Satoh et al. |
| 7,519,218 B2 | 4/2009 | Takemoto et al. |
| 7,626,596 B2 | 12/2009 | Kotake et al. |
| 7,791,618 B2 | 9/2010 | Endo et al. |
| 7,848,903 B2 | 12/2010 | Aratani et al. |
| 8,350,897 B2 | 1/2013 | Endo et al. |
| 8,730,234 B2 | 5/2014 | Iizuka et al. |
| 9,324,148 B2 | 4/2016 | Ishikawa et al. |

(Continued)

FOREIGN PATENT DOCUMENTS

JP       2014-140716 A       8/2014

*Primary Examiner* — Menatoallah Youssef
(74) *Attorney, Agent, or Firm* — Venable LLP

(57) ABSTRACT

An image processing apparatus, comprises an image acquiring unit that acquires a plurality of object images captured by imaging an object for a plurality of times; a shape acquiring unit that acquires shape information, which is information representing a shape of the object; an image dividing unit that divides each of the plurality of object images into at least two partial images, based on the shape information; and an image registering unit that registers the divided partial images.

13 Claims, 12 Drawing Sheets

(56) References Cited

U.S. PATENT DOCUMENTS

| | | | |
|---|---|---|---|
| 9,767,562 B2 | 9/2017 | Takama et al. | |
| 9,808,213 B2 | 11/2017 | Endo et al. | |
| 2010/0256496 A1* | 10/2010 | Zhu | A61B 5/0091 |
| | | | 600/459 |
| 2015/0070469 A1 | 3/2015 | Yoshibayashi et al. | |
| 2015/0265251 A1* | 9/2015 | Cho | A61B 8/0825 |
| | | | 600/437 |
| 2015/0351639 A1 | 12/2015 | Abe | |
| 2017/0039776 A1 | 2/2017 | Endo et al. | |
| 2017/0337694 A1 | 11/2017 | Takama et al. | |

\* cited by examiner

IMAGE PROCESSING APPARATUS AND IMAGE PROCESSING METHOD

BACKGROUND OF THE INVENTION

Field of the Invention

The present invention relates to an apparatus that processes an image acquired by imaging an object.

Description of the Related Art

Research on imaging structural information inside an object and on biological information, that is, functional information, is ongoing in medical fields. Photoacoustic tomography (PAT) is one such technique that has been proposed.

If light, such as laser light, is irradiated to a living body, which is an object, an acoustic wave (typically an ultrasound wave) is generated when the light is absorbed by a biological tissue inside the object. This phenomenon is called the "photoacoustic effect", and the acoustic wave generated by the photoacoustic effect is called a "photoacoustic wave". The tissues constituting the object have different absorption rates of the light energy, hence the generated photoacoustic waves also have different sound pressures. With PAT, a generated photoacoustic wave is received by a probe, and the received signal is mathematically analyzed, so as to acquire characteristic information inside the object.

In the photoacoustic imaging, one image (hereafter "shot image") is generated from a photoacoustic wave which is observed in one execution of light irradiation. In some cases, in order to reduce noise and expand an imaging range, light is irradiated for a plurality of times, and a series of shot images, acquired by each light irradiation, are combined and generated as an image of the object (hereafter "integrated image").

However, if the object moves during the plurality of times of light irradiations, the same segment of the object may be deviated and recorded in each shot image. In other words, displacement is generated among each shot image. If the displaced shot images are combined, the quality of the integrated image drops.

A known technique to solve this problem is to estimate the displacement amount (motion vector) among each shot image by comparing the plurality of shot images, and to register the shot images (Japanese Patent Application Publication No. 2014-140716).

SUMMARY OF THE INVENTION

However, in the case of the displacement correcting method according to Japanese Patent Application Publication No. 2014-140716, the registration precision may not be sufficient. In other words, a further improvement in registration precision is demanded.

With the foregoing problem of the prior art in view, it is an object of the present invention to obtain higher precision in an image processing apparatus that combines a plurality of object images.

The present invention in its one aspect provides an image processing apparatus, comprising an image acquiring unit that acquires a plurality of object images captured by imaging an object for a plurality of times; a shape acquiring unit that acquires shape information, which is information representing a shape of the object; an image dividing unit that divides each of the plurality of object images into at least two partial images, based on the shape information; and an image registering unit that registers the divided partial images.

The present invention in its another aspect provides an image processing method, comprising acquiring a plurality of object images captured by imaging an object for a plurality of times; acquiring shape information, which is information to represent a shape of the object; dividing each of the plurality of object images into at least two partial images, based on the shape information; and registering the divided partial images.

According to the present invention, a further higher precision can be obtained in the image processing apparatus that combines a plurality of object images.

Further features of the present invention will become apparent from the following description of exemplary embodiments with reference to the attached drawings.

DESCRIPTION OF THE EMBODIMENTS

Figure 1:
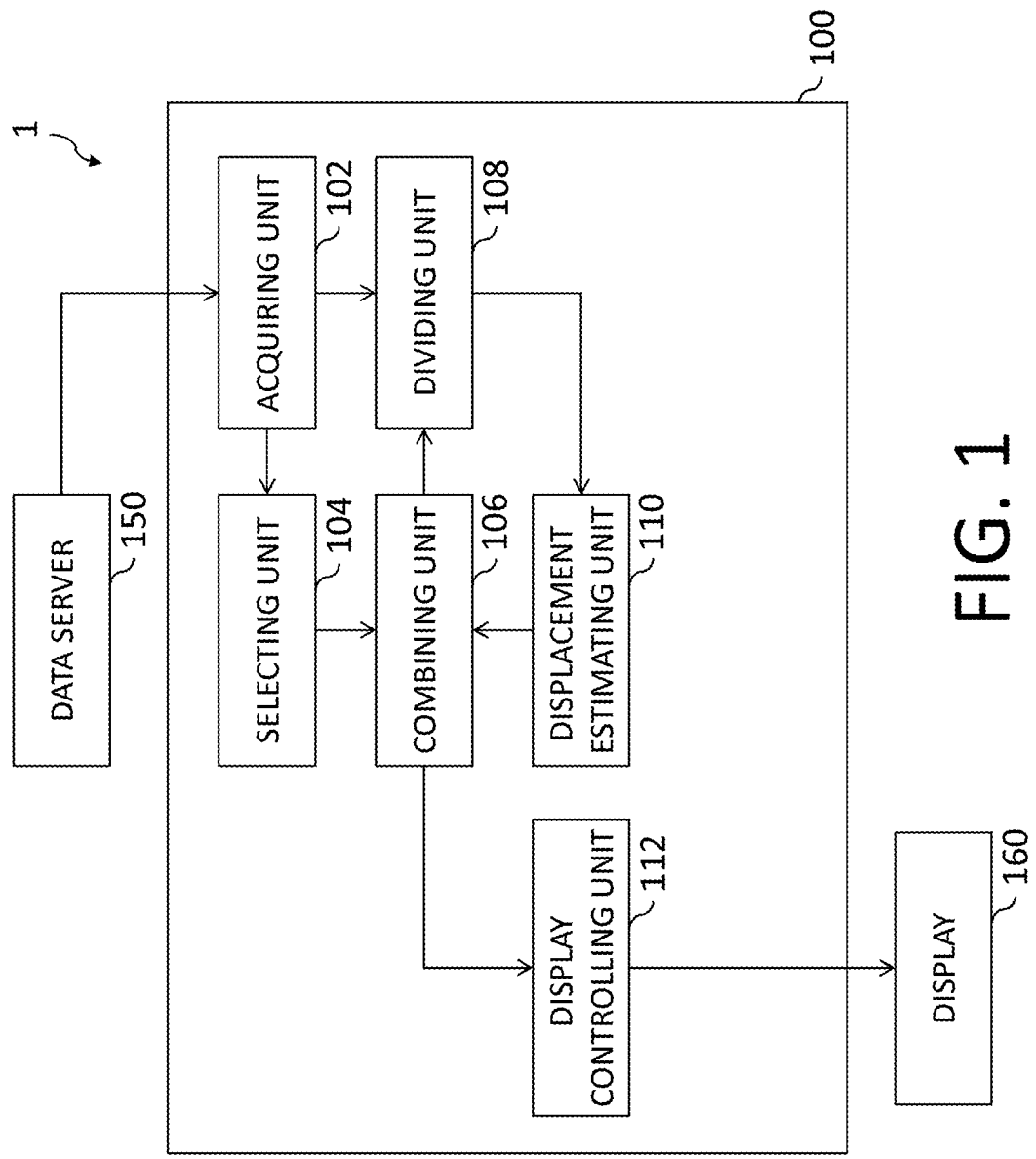
FIG. 1 is a diagram depicting functional blocks of an image processing apparatus according to Embodiment 1.

Preferred embodiments of the present invention will be described with reference to the drawings. Dimensions, materials, shapes, relative dispositions of the components, and the like, described below can be appropriately changed depending on the configuration and various conditions of the apparatus to which the invention is applied. Therefore the following description is not intended to limit the scope of the present invention.

The image processing apparatus of the present invention can be applied to an apparatus utilizing the photoacoustic effect which irradiates an object with light (electromagnetic wave), receives an acoustic wave generated inside the object, and acquires characteristic information on the object as image data. In this case, the characteristic information is information on characteristic values which are generated using receive signals obtained by receiving the photoacoustic wave, and which correspond to a plurality of positions inside the object respectively.

The characteristic information acquired by the photoacoustic measurement are values reflecting the absorption rates of the light energy. For example the characteristic information includes a generation source of the acoustic wave generated by the light irradiation, the initial sound pressure inside the object, or the light energy absorption density, or the absorption coefficient derived from the initial sound pressure, and the concentration of the substance constituting the tissue. By determining the oxyhemoglobin concentration and the deoxyhemoglobin concentration as the substance concentration, oxygen saturation degree distribution can be calculated. Glucose concentration, collagen concentration, melanin concentration and volume fractions of fat and water can also be determined.

Based on the characteristic information at each position inside the object, a two-dimensional or three-dimensional characteristic information distribution can be acquired. The distribution data can be generated as image data. The characteristic information may be determined as distribution information at each position inside the object instead of as numeric data. Examples of the distribution information are, the initial sound pressure distribution, the energy absorption density distribution, the absorption coefficient distribution, and the oxygen saturation distribution.

The acoustic wave in the present description is typically an ultrasound wave, including an elastic wave called a "sound wave" and an acoustic wave. An electric signal, which was converted from an acoustic wave by a probe or the like, is called an "acoustic signal". Such phrases as the ultrasound wave or the acoustic wave in the present description, however, are not intended to limit the wavelengths of these elastic waves. An acoustic wave generated by the photoacoustic effect is called a "photoacoustic wave" or a "light-induced ultrasound wave". An electric signal, which originates from a photoacoustic wave, is called a "photoacoustic signal". An electric signal, which originates from an ultrasound echo, is called an "ultrasound signal".

Embodiment 1

<System Configuration>

An image processing apparatus according to Embodiment 1 is an apparatus which generates an integrated image by combining a plurality of shot images of a human object (human breast in Embodiment 1) captured in a time series. To combine the plurality of shot images, each shot image is divided into a plurality of sub-images (divided images), and the sub-images are registered, rather than simply adding the shot images.

FIG. 1 is a functional block diagram depicting a configuration of an image processing system according to Embodiment 1.

The image processing system 1 according to Embodiment 1 is a system which includes an image processing apparatus 100, a data server 150 and a display 160.

The image processing apparatus 100 includes an acquiring unit 102, a selecting unit 104, a combining unit 106, a dividing unit 108, a displacement estimating unit 110 and a display controlling unit 112.

In the image processing system according to this embodiment, the data server 150 holds the captured images of an object and information on the object, and supplies this data to the image processing apparatus 100.

In concrete terms, the data server 150 stores: (1) images acquired by capturing an image of the object for a multiple times (hereafter "shot images"); (2) data representing the surface shape of the object (the shape information according to the present invention, hereafter "surface shape data"); and (3) information which represents the distance from the object surface to the later mentioned dividing position, and which is used for processing the image (hereafter "distance data"), and sends this information to the image processing apparatus 100 when requested.

The data stored in the data server 150 will be described first.

<Shot Image>

In this embodiment, volume data storing values, which correspond to three-dimensionally arrayed voxels respectively, is used for an object image (shot image). The shot image can also be called a "three-dimensional volume data", a "three-dimensional image", or a "three-dimensional tomographic image". In this embodiment, the shot image is three-dimensional data, but the shot image may be two-dimensional data. "Object image" refers to an image representing an object.

A series of shot images includes such supplementary information as a size of the image, resolution, imaging parameters, and position information of a transmitting/receiving unit upon imaging (hereafter "probe", in which a unit to irradiate the object with pulsed light, and a unit to receive the photoacoustic wave, are integrated). The shot image that is processed in this embodiment is generated by emitting light and receiving the photoacoustic wave for a plurality of times at each predetermined position, while mechanically moving the probe to the position, and acquiring signals.

This embodiment is described based on the assumption that a three-dimensional spatial distribution (initial sound pressure distribution) of the generated sound pressure (initial sound pressure) of the photoacoustic wave is acquired as the shot image of the object. In the following description, the i-th shot image is denoted by $I_s\_i$ ($1 \le i \le N$, i is a positive integer, N is a total number of shots). A voxel value included in the shot image is denoted by a functional expression, that is, $I_s\_i$ (x, y, z).

Figure 2:
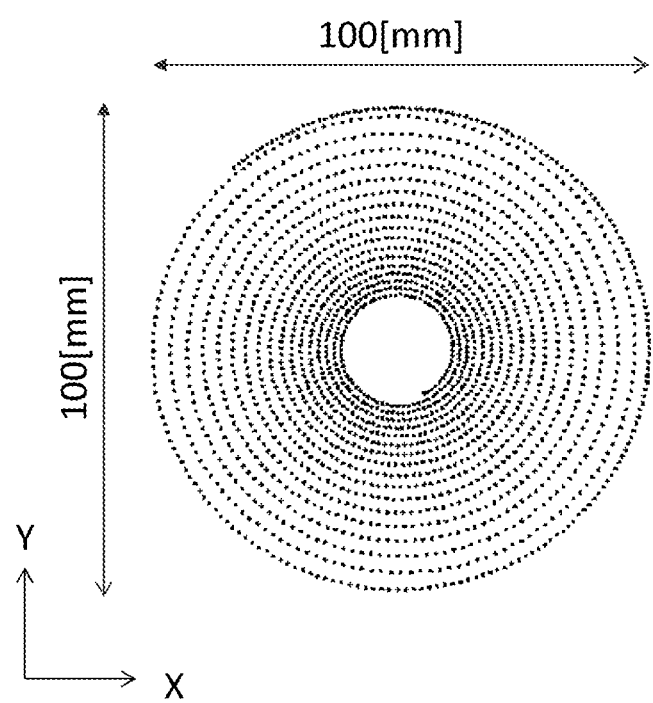
FIG. 2 is a diagram depicting positions of a probe when light is irradiated.

FIG. 2 is a diagram depicting positions of the probe when light is irradiated. Each point in FIG. 2 is generated by plotting the position of the probe at each light irradiation. The probe emits light N times while changing positions, and receives the photoacoustic wave at N locations. In FIG. 2, light is irradiated 2050 times, and the probe moves a distance of about 1.5 mm on average between light irradiations.

Figure 3:
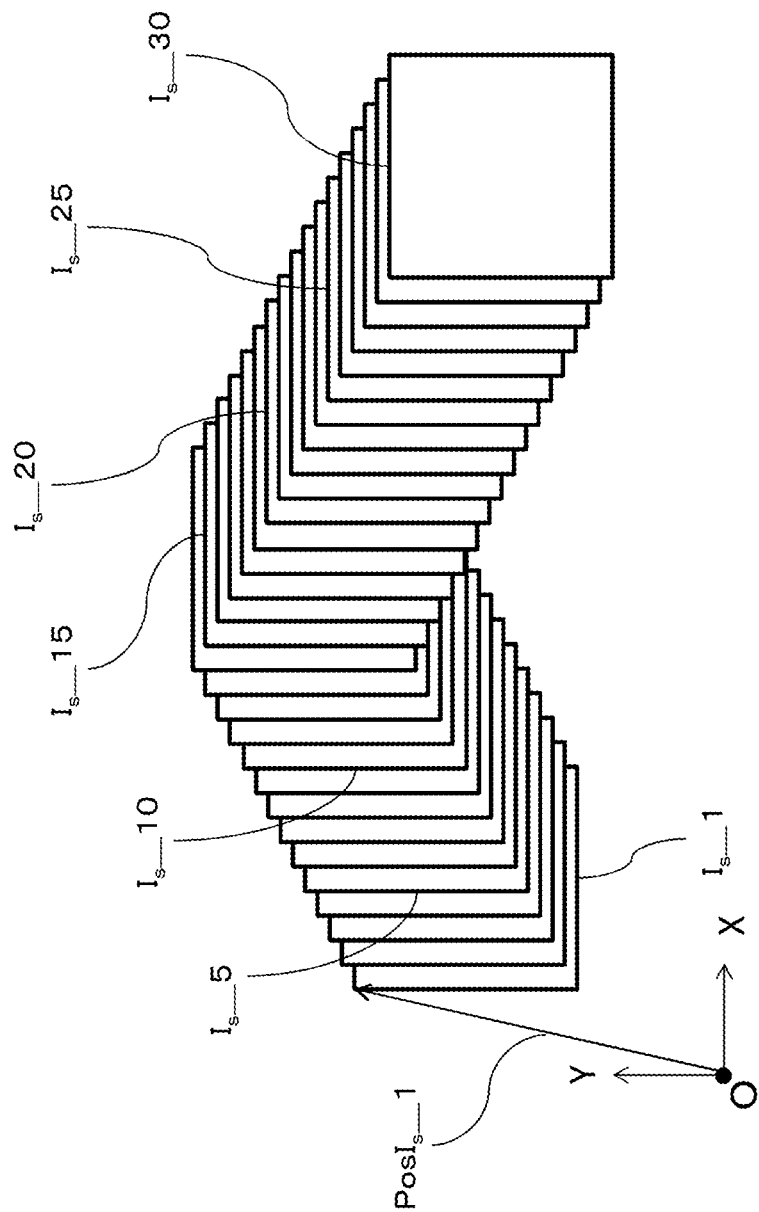
FIG. 3 is a diagram depicting shot images according to Embodiment 1.

FIG. 3 is a diagram depicting 30 shot images ($I_s\_1$ to $I_s\_30$) acquired by imaging an object. A shot image in this embodiment is a three-dimensional volume data, but each shot image here is expressed by an XY plane to make description easier. In this embodiment, the size of a shot image acquired by one execution of light irradiation is assumed to be a 60 mm³ cubic region.

In this case, a size of a shot image (60 mm) that is acquired by one execution of light irradiation is larger than a moving distance (1.5 mm) of the probe 200 between executions of light irradiation. Therefore as illustrated in FIG. 3, at least two shot images, which were continuously acquired, overlap with each other.

Here the position of each shot image is assumed to be a position at the upper left corner of each shot image (a position where the X coordinate value is the minimum, and the Y coordinate is the maximum in FIG. 3) with respect to the reference position O.

If the position representing the probe and the position representing the shot image are different, the coordinates may be appropriately converted.

In FIG. 3, the position PosI$_s$_1 of the shot image I$_s$_1 is shown as an example. As illustrated in FIG. 2, the position of the probe is different for each execution of light irradiation, hence each shot image is at a mutually different position with respect to the reference position O.

In the configuration of this embodiment described above, the probe is mechanically moved, but the user may hold and move the probe to capture an image. In this case, the position of the probe (position corresponding to each shot image) may be measured using a position sensor installed in the probe, for example. In each of the plurality of times of light irradiation, a shot image corresponding to a same region may be acquired, and an integrated image may be generated by combining these shot images.

<Surface Shape Data and Distance Data>

The surface shape data represents the shape of the surface of an object which is imaged, and is represented by point cloud data, for example. The surface shape data can be acquired by an arbitrary measurement method. For example, the shape of the surface of the object (e.g. skin) can be acquired by transmitting an ultrasound wave to the object, and analyzing the reflected wave. The shape may be acquired by optically measuring the object using an infrared light or the like.

If the holding member (e.g. holding plate, holding cup) to hold the object is used, the information representing the shape of this member may be held in advance, and read and used as the surface shape data. Further, the shape of the member to hold the object may be measured, and regarded as the surface shape of the object.

The distance data represents the distance from the surface of the object to the dividing position. The distance data will be described later when the division of the image is described.

The shot image, the surface shape data, and the distance data described above, are transmitted from the data server 150 to the image processing apparatus 100 when requested by the image processing apparatus 100.

The configuration of the image processing apparatus 100 will be described next.

The acquiring unit 102 (the image acquiring unit and the shape acquiring unit according to the present invention) is a unit to acquire a plurality of shot images, the surface shape data and the distance data from the data server 150 for the target object.

The selecting unit 104 is a unit to select at least two shot images corresponding to temporarily continuous light irradiation executions from a plurality of acquired shot images.

The combining unit 106 (the image generating unit according to the present invention) is a unit to generate a group image by combining the shot images selected by the selecting unit 104. The combining unit 106 is also a unit to generate an integrated image by combining divided images that are divided by the later mentioned dividing unit 108.

The dividing unit 108 (the image dividing unit according to the present invention) is a unit to divide each group image generated by the combining unit 106 into two divided images based on the acquired distance data.

The displacement estimating unit 110 is a unit to estimate the displacement amount between images divided by the dividing unit 108.

The contents of the concrete processing performed by the selecting unit 104, the combining unit 106, the dividing unit 108, and the displacement estimating unit 110 will be described later.

The display controlling unit 112 is a unit to control the output of screen images to notify information to the user, including a series of shot images, group images, divided images and integrated images to the display 160.

The image processing apparatus 100 can be constructed as an information processing apparatus, that includes a CPU, a main storage device, and an auxiliary storage device. Each unit illustrated in FIG. 1 functions when the program stored in the auxiliary storage device is loaded to the main storage device, and executed by the CPU. All or a part of the illustrated functions may be executed by a circuit (e.g. semiconductor integrated circuit) designed for dedicated use.

An example when the image processing apparatus 100 is constructed as the image processing apparatus will be described.

Figure 4:
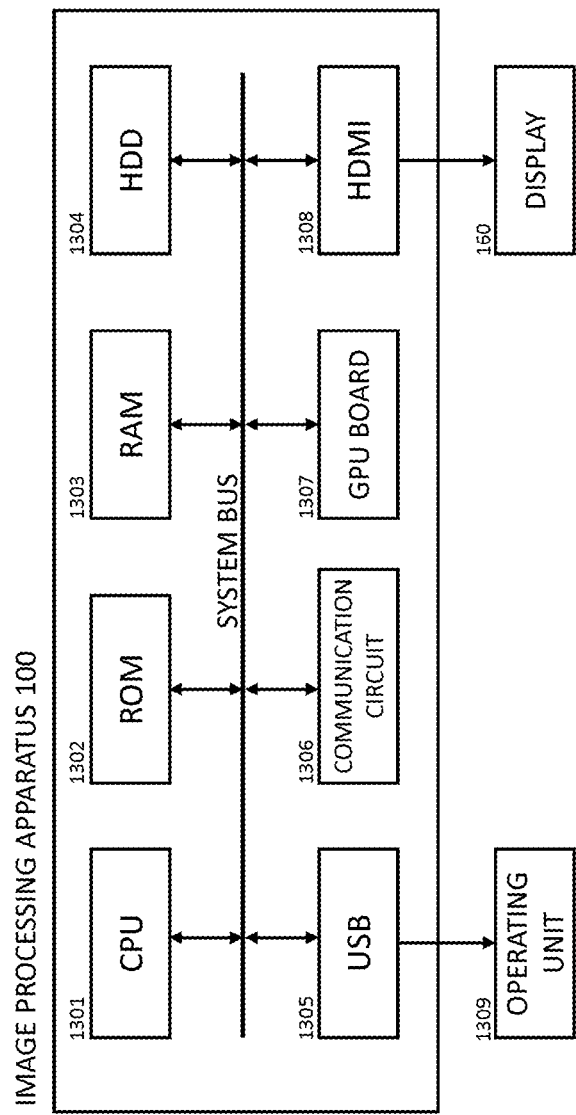
FIG. 4 is a diagram depicting a hardware configuration of the image processing apparatus according to the present invention.

FIG. 4 is a diagram depicting an example of the hardware configuration of the image processing apparatus 100. The image processing apparatus 100 includes a CPU 1301, a ROM 1302, a RAM 1303, an HDD 1304, a USB 1305, a communication circuit 1306, a GPU board 1307 and an HDMI® 1308. These components are communicably connected via a system bus.

The CPU 1301 is a control circuit to integrally control the image processing apparatus 100 and each unit connected thereto. The CPU 1301 performs control by executing a program stored in the ROM 1302. The CPU 1301 also executes the display driver, which is software to control the display 160, so as to perform the display control for the display 160. Furthermore, the CPU 1301 performs the input/output control for the operating unit 1309.

The ROM 1302 is a memory to store programs for executing control procedures by the CPU 1301, and to store data.

The RAM 1303 is a memory to store programs for executing processing of the image processing apparatus 100 and each unit connected thereto, and various parameters used for the image processing. The RAM 1303 stores a control program executed by the CPU 1301, and temporarily stores various data which the CPU 1301 uses to execute various controls.

The HDD 1304 is an auxiliary storage device to store shot images, surface shape data and other various data. The USB 1305 is an interface to connect the operating unit 1309.

The communication circuit 1306 is a circuit to communicate with each unit constituting the image processing system 1. The communication circuit 1306 may be constituted by a plurality of devices in accordance with the desired communication format.

The GPU board 1307 is a general purpose graphics board which includes a GPU and a video memory. Inclusion of the GPU board 1307 allows computing image processing and image display at high-speed without a requirement of dedicated hardware. If the data server 150 can perform image combining processing and the like, then the image processing apparatus 100 need not include the GPU board 1307.

HDMI® 1308 is a video interface to connect the display 160.

<Processing Flow Chart>

The processing performed by the image processing apparatus 100 will be described next, with reference to the processing flow chart in FIG. 5.

First in step S210, the acquiring unit 102 acquires a plurality of shot image I$_s$_i (1≤i≤N) stored in the data server 150. The shot images acquired here are N number of images captured by N times of light irradiation. In this step, position information corresponding to each shot image is acquired as well.

Then in step S220, the selecting unit 104 selects at least two shot images corresponding to temporarily continuous light irradiation executions from the plurality of acquired shot images. At least two shot images selected here are collectively called the "first group data $G_g\_1$".

Further, the selecting unit 104 selects at least two shot images corresponding to temporarily continuous light irradiation executions. The combination of these shot images is different from that of the first group data, and these shot images include a part of the shot images included in the first group data. At least two shot images selected here are collectively called the "second group data $G_g\_2$".

The selecting unit 104 generates a plurality of group data using the same method.

In the following description, the j-th group data is denoted by $G_g\_j$ ($1 \le j \le M$) (M is a total number of groups). An item to which the subscript j is attached indicates that this item corresponding to the j-th group data. j is a positive integer, and is also called a "group index". An item to which the subscript g is attached indicates that this item corresponds to one group data.

Figure 6:
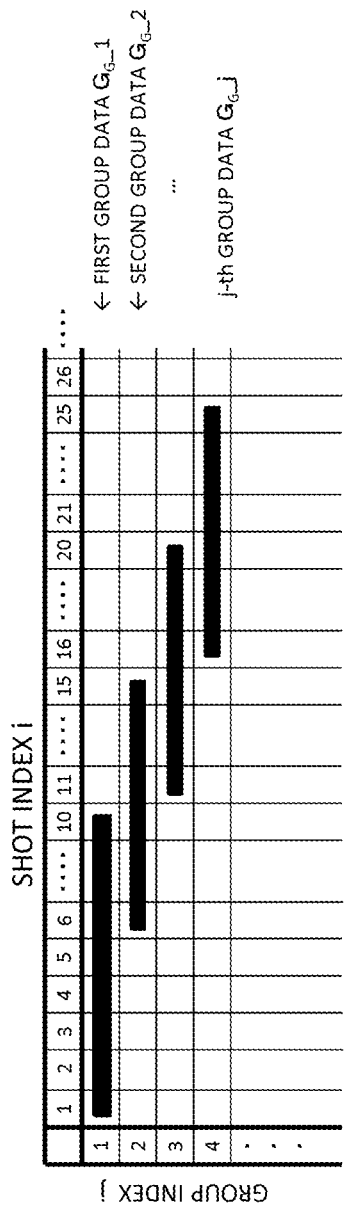
FIG. 6 is a diagram depicting a method of selecting group data according to Embodiment 1.

The method of selecting the group data will be described next with reference to FIG. 6.

In this example, the selecting unit 104 selects ten shot images $I_s\_1$ to $I_s\_10$, which correspond to the first to tenth light irradiation executions, as the first group data $G_g\_1$. The selecting unit 104 also selects ten shot images $I_s\_6$ to $I_s\_15$, which correspond to the sixth to fifteenth light irradiation executions, as the second group data $G_g\_2$. In this example, the shot images, which correspond to the sixth to tenth light irradiation executions, are selected as mutually overlapping shot images.

In this way, according to this example, the selecting unit 104 selects shot images corresponding to ten times of light irradiation, with shifting the start point by five times of light irradiation each time, whereby a plurality of group data $G_g\_1$ to $G_g\_M$ are generated. In other words, the j-th group data is a group of (5j−4)th to (5j+5)th shot images.

In the case of this example, each group data constituted by ten shot images is generated with shifting five shot images at a time. Therefore a number of shot group data (M) is smaller than the number of shot images (N). For example, if the number of shot images is N=2050, the number of group data is M=409.

The group data may be generated by a method other than the above. For example, the number of shot images constituting the group data need not be ten. The number of shot images which overlap need not be five either. The shot images need not overlap. Further, the number of shot images constituting a group data may be variable. For example, the number of shot images may be determined based on the positions of the shot images, so that the later mentioned size of the group image is within predetermined values. The number of shot images may be dynamically set based on the acquired image quality. For example, a number of shot images, by which a predetermined final image quality can be acquired, may be selected. The number of shot images constituting the group data may be one. This is equivalent to using each shot image as a group image respectively. In this case, the processing operations in steps S220 and S230 can be omitted.

Then in step S230, the combining unit 106 combines the plurality of shot images included in the group data, and acquires the combined image (called a "group image") for each group data.

Here a group image acquired by combining the j-th group data $G_g\_j$ is denoted by $I_g\_j$. The combining processing to acquire a group image is called a "first combining".

Figure 7A:
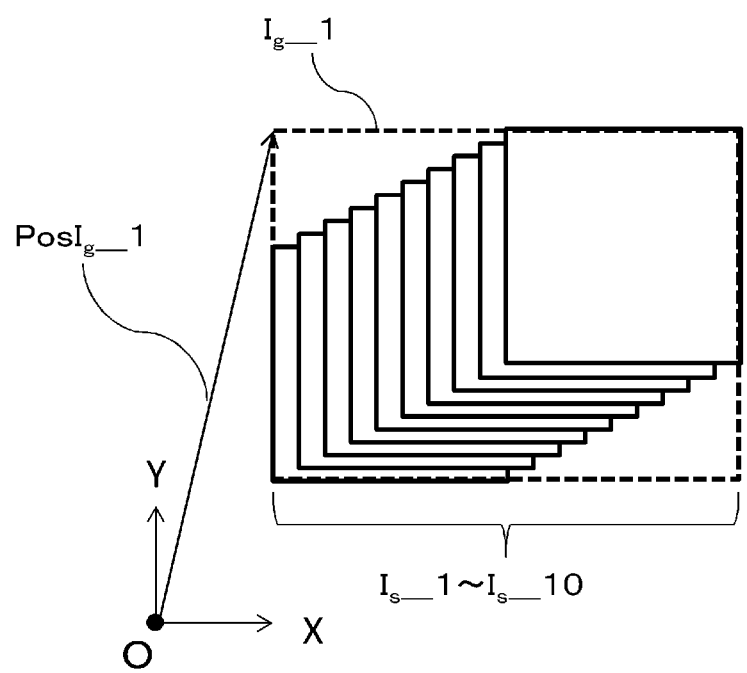
FIG. 7A is a diagram depicting a group image according to Embodiment 1.

FIG. 7A is a diagram depicting a first group image $I_g\_1$ which is acquired by combining ten shot images included in the first group data $G_g\_1$. Here a rectangular region, having a minimum area which includes all the shot images to be combined, is assumed to be a region of the group image. Just like the case of the shot image, the coordinates at the upper left corner of the group image are assumed to be position $PosI_g\_j$ of the group image.

Figure 7B:
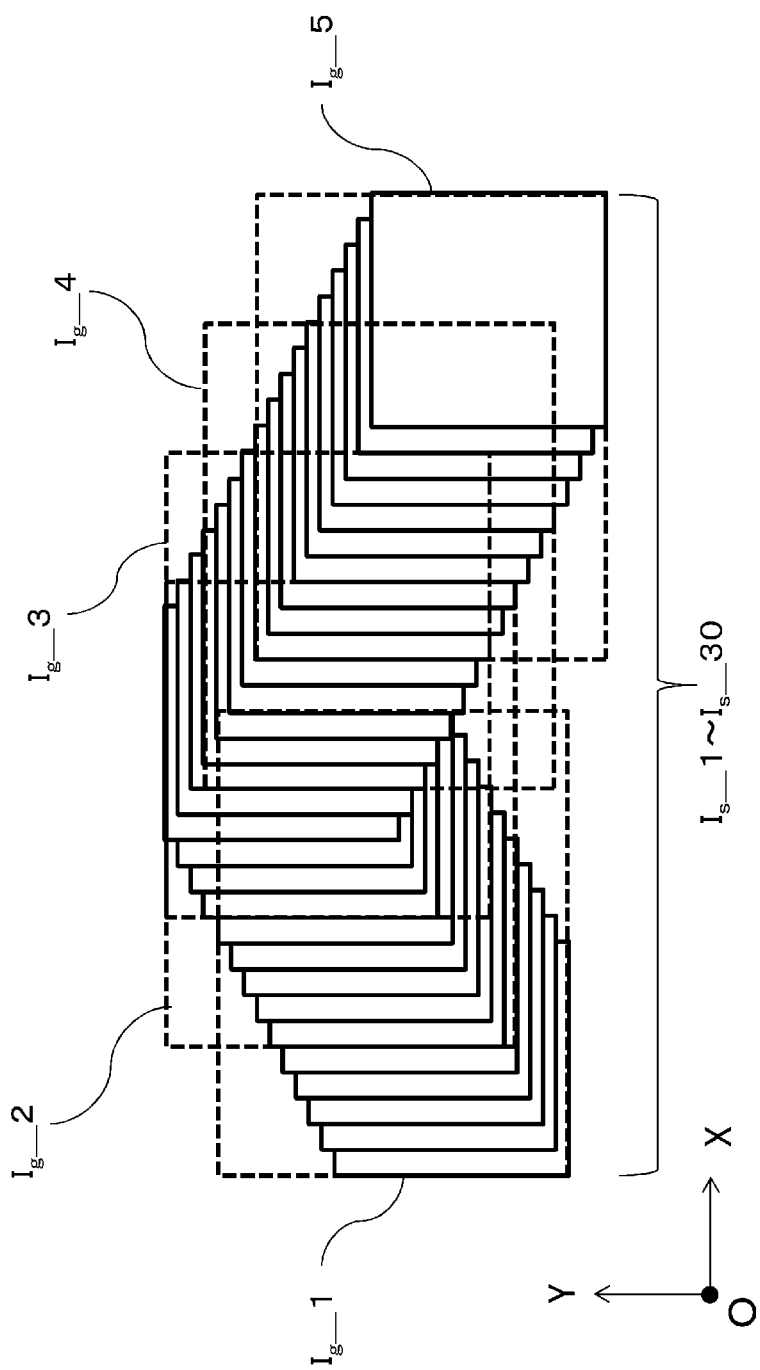
FIG. 7B is a diagram depicting a group image according to Embodiment 1.

FIG. 7B is a diagram depicting five group images ($I_g\_1$ to $I_g\_5$) generated by combining ten shot images included in the first to fifth group data respectively. In FIG. 7B, the solid lines indicate each shot image, and the broken lines indicate each group image.

Figure 7C:
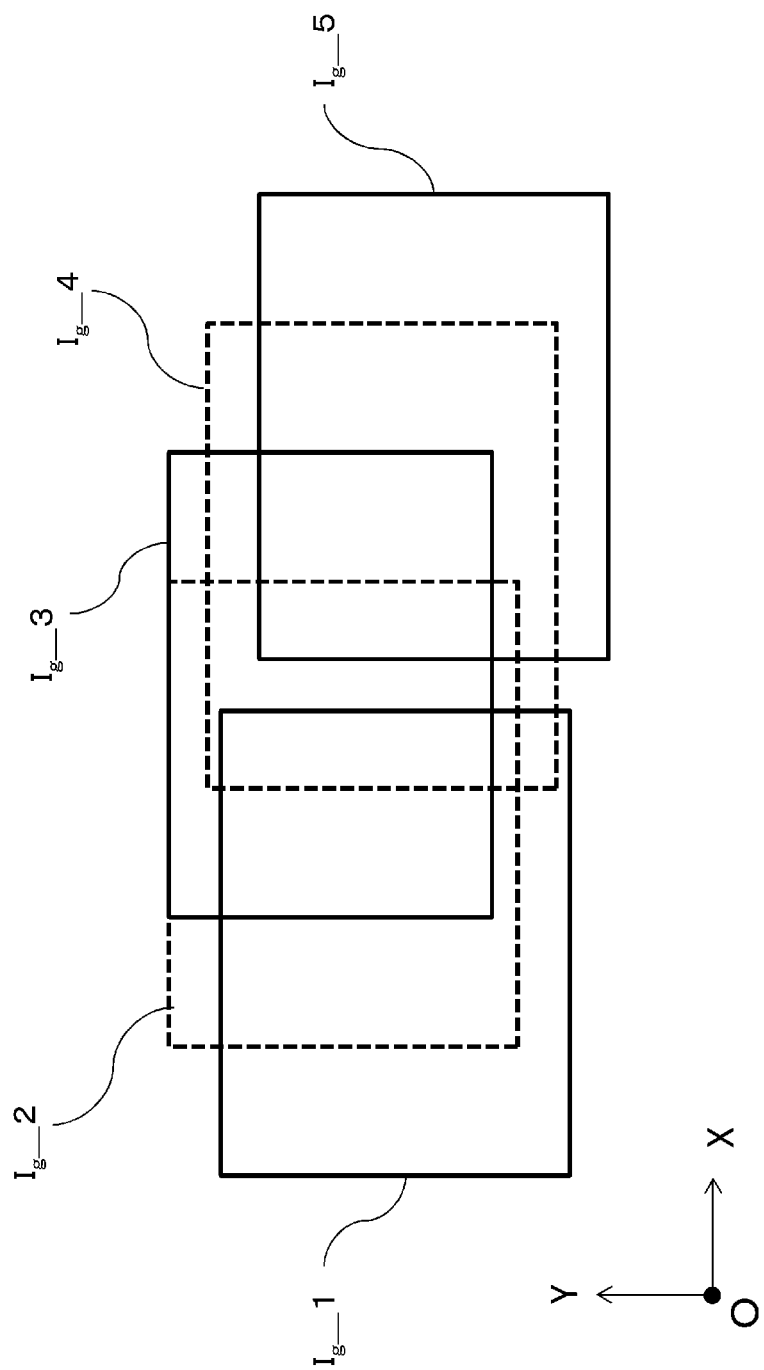
FIG. 7C is a diagram depicting a group image according to Embodiment 1.

FIG. 7C is a diagram when only the group images $I_g\_1$ to $I_g\_5$ are extracted from FIG. 7B. The solid lines indicate the group images $I_g\_1$, $I_g\_3$ and $I_g\_5$, and the broken lines indicate $I_g\_2$ and $I_g\_4$.

In this embodiment, the group image is generated by averaging the selected shot images (hereafter "averaging processing"). To perform averaging processing, for each voxel of the group image in a region where each shot image overlaps, the voxel value of each shot image at a position corresponding to this voxel is added, and the result is divided by a number of overlapped shot images.

When the shot images are combined, a weight image $W_g\_j$ (x, y, z), which represents the distribution of reliability, may be generated together with the group image $I_g\_j$. The weight image $W_g\_j$ is a volume data which represents a number of overlapped shot images (a value used for division in the case of the averaging processing) at each position in the group image $I_g\_j$. If many shot images are combined in a region among the regions included in the group image, the reliability of the values in this region is regarded as high. Hence the weight image $W_g\_j$ may be generated as an image representing the distribution of the reliability in the group image.

When the shot images are combined, the weighting may be performed in advance for each of the target shot images. Further, the shot images may be combined after removing the regions containing considerable noise using an outlier removal method or the like.

The combining method is not limited to the averaging processing. Various methods may be used, as long as volume data, which represent the characteristics of the object more accurately than an individual shot image, can be acquired. Processing to correct a shift in the relative position of the object and the receiving unit among the light irradiation executions (e.g. processing to correct displacement of the object by adjusting the positions of the shot images) is not included in the combining processing described in the present description.

By performing the above mentioned combining processing, the noise included in each shot image can be reduced, and an image which more accurately reproduces the characteristics of the object can be acquired. Particularly by selecting shot images which are temporarily continuous in step S220, the group image, in which the influence of a position shift of the object is minimized, can be generated.

By performing the processing operations up to step S230, an image, of which quality is higher than an individual shot image, can be generated. However, in reality, the relative positional relationship between the object and the probe shifts while the light irradiation is executed for a plurality of times, and the quality of the group image may drop because of this shift. Hence, in the image processing apparatus according to Embodiment 1, additional image registration is performed for the group image, so as to prevent a drop in quality.

The image registering processing (steps S235 to S270) will be described in detail.

First in step S235, the dividing unit 108 divides each of the group image combined in step S230 into a plurality of images in accordance with the distance from the surface of the object.

If the object is a breast, the region close to the surface of the breast (hereafter "shallow region"), of which distance from the surface of the breast is less than 10 mm, is a subcutaneous fat layer, and a region which is distant from the surface of the breast (hereafter "deep region"), of which distance from the surface of the breast is at least 10 mm, is a mammary gland layer. The compositions of these layers are completely different. Therefore in this embodiment, each of the plurality of group images is divided into two by a boundary between the shallow region (subcutaneous fat layer) and the deep region (mammary gland layer). The deep region is a region located more distant from the surface of the breast than the shallow region.

The region of which distance from the surface of the breast is at least 40 mm is a chest wall, and composition thereof is completely different from those of the subcutaneous fat layer and the mammary gland layer. Therefore the group image may be divided by the boundary between the mammary gland layer and the chest wall. Further, the group image may be divided into three by the boundary between the subcutaneous fat layer and the mammary gland layer, and by the boundary between the mammary gland layer and the chest wall. Furthermore, the group image may be divided into four or more based on other standards.

Figure 8:
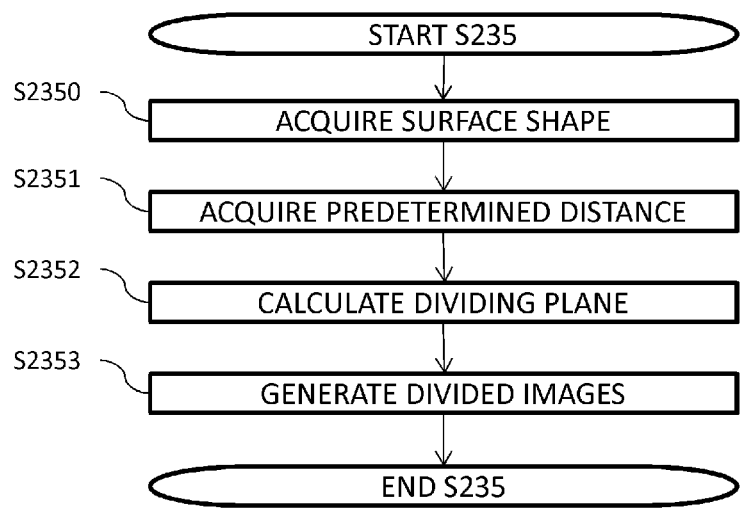
FIG. 8 is a flow chart depicting an image dividing processing according to Embodiment 1.

FIG. 8 is a flow chart depicting the processing performed in step S235 in more detail.

First in step S2350, the acquiring unit 102 acquires the surface shape data corresponding to the object from the data server 150.

Here the surface shape data of the object may be acquired from the image which was acquired in advance by combining shot images, without correcting the displacement, using a known image processing method, for example. If an image of which displacement has been corrected to a certain extent by a known method is available, the surface shape data of the object may be acquired based on this image.

The processing to acquire the surface shape data of an object based on each shot image may be performed by the acquiring unit 102 in this step. In this case, the data server 150 need not hold the surface shape data of the object.

Then in step S2351, the acquiring unit 102 acquires the distance data (data representing the distance from the surface of the object to the dividing position) from the data server 150. For example, if the value indicated by the distance data is 10 mm, the image is divided at a 10 mm depth from the surface of the object. The distance data need not be provided from the data server 150, and the acquiring unit 102 may hold the distance data in advance.

At least one value may be selected from a plurality of values in accordance with the dividing method. For example, in the case of dividing the image into "the subcutaneous fat layer and the mammary gland layer", a value of 10 mm may be selected, and in the case of dividing the image into "the mammary gland layer and the chest wall", a value of 40 mm may be selected. In the case of dividing the image into "the subcutaneous fat layer, the mammary gland layer and the chest wall", two values, 10 mm and 40 mm, may be selected.

The dividing method may be set in advance, or may be inputted by the user via the operating unit 1309. The value of the distance data need not be a fixed value, but may be adjusted appropriately in accordance with the object. For example, the size of the breast (object) may be inputted so that the value is set in accordance with the size. Or for example, the size of the breast may be selected from several levels, so that a value in accordance with the selected size range is read and used.

Further, the value to be used may be determined based on clinical information (e.g. gender, weight, height, body fat percentage) of the object.

Then in step S2352, the dividing unit 108 calculates a plane to divide each group image (dividing plane) based on the surface shape data and the distance data of the object.

Figure 9:
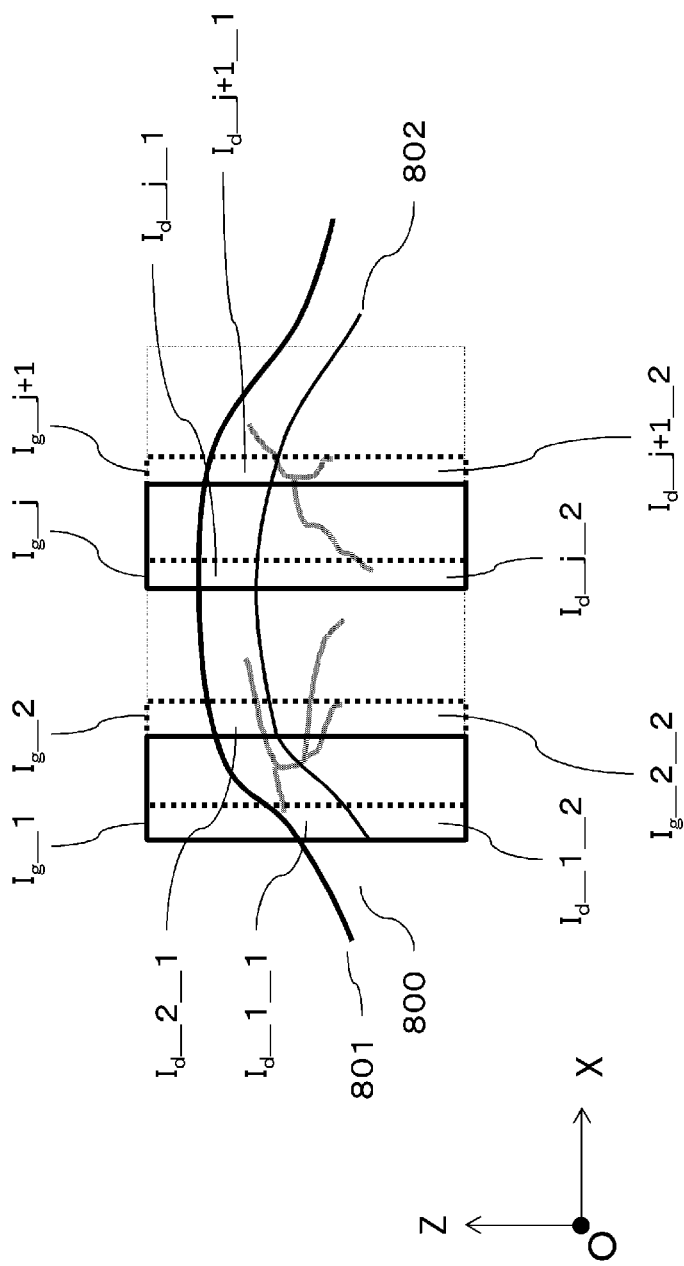
FIG. 9 is a diagram depicting the surfaces that divide a group image.

FIG. 9 is a diagram depicting the dividing plane. Here an equivalent surface (curved surface) 802, of which distance from the surface 801 of the object 800 is a predetermined distance (10 mm in this embodiment), is calculated by a known method, and this curved surface is determined as the dividing plane.

The group image and the divided image are three-dimensional volume data, but the group image and the divided images are regarded as two-dimensional data in FIG. 9 so that description is easier.

In each group image, a partial curved surface constituting the curved surface 802 may be approximated by a plurality of planes, and these planes may be determined as the dividing plane.

A partial curved surface may be approximated by planes of which normal line directions match with the Z axis in FIG. 9, so that each divided image becomes a rectangular parallelepiped, and these planes may be determined as the dividing plane. In FIG. 9, the object 800 is a breast in the position when the patient is in the face down position, and a state of rotating 180° around the Y axis. In other words, the gravity direction is the positive direction of the Z axis. However, the patient's position is not limited to face down, but may be any position, such as face up or sitting.

Then in step S2353, the dividing unit 108 divides each group image at the dividing plane, and generates divided images. The p-th image, out of the divided images generated by dividing the j-th group image $I_g\_j$ by P, is denoted by $I_d\_j\_p$ (1≤p≤P). Here a case of P=2 will be described.

In the example in FIG. 9, the dividing unit 108 divides a group image $I_g\_1$ into a divided image $I_d\_1\_1$ and a divided image $I_d\_1\_2$. A group image $I_g\_2$ is divided into a divided image $I_d\_2\_1$ and a divided image $I_d\_2\_2$. In the same manner, each group image $I_g\_j$ is divided into a divided image $I_d\_j\_1$ and a divided image $I_d\_j\_2$.

In the case of FIG. 9, a divided image corresponding to the shallow region and a divided image corresponding to the deep region do not overlap (that is, the divided images are completely separated by the dividing plane as the boundary plane), but images may overlap. In other words, predetermined regions on either side of the dividing plane may be included in both the divided images.

The size of the divided image corresponding to the shallow region and the size of the divided image corresponding to the deep region may be the same size as the group image before dividing. In this case, the pixel values in unnecessary regions may be deleted (set to 0). Further, the pixel values in a region outside the surface 801 (a region corresponding to outside the body) may be set to 0. This can prevent performing meaningless processing for unnecessary regions in the later mentioned steps.

For the divided image, the position thereof can be defined in the same manner as the shot image and the group image. For example, the coordinates of the edge of the region can be used, but if the divided image is not rectangular, other coordinates (e.g. coordinates of center of gravity) may be used. In this embodiment, the position of the divided image $I_d\_j\_p$ is defined as $PosI_d\_j\_p$.

Just like the group image, the weight image $W_d\_j\_p$ (x, y, z), which represents the distribution of the reliability, may be generated for the divided image as well. The weight image $W_d\_j\_p$ is a volume data that is acquired by performing the dividing processing on the weight image $W_g\_j$, in the same manner as the dividing processing performed on the group image. The partial weight image $W_d\_j\_p$ is an image representing the distribution of the reliability in the divided image.

The above is the description of step S235.

Referring back to FIG. 5, the flow chart will continue to be described.

In step S240, the displacement estimating unit 110 selects a pair of divided images that satisfy a predetermined condition, out of the plurality of divided images acquired in step S235.

The predetermined condition is, for example, that at least a predetermined volume of an overlapped region is included. Thereby comparison of unrelated divided images can be prevented in the later mentioned step S250, which can reduce redundant calculation.

In step S240, a pair of $I_d\_1\_1$ and $I_d\_2\_1$, a pair of $I_d\_j\_2$ and $I_d\_j+1\_2$ and the like in FIG. 9 are selected. This is because these pairs overlap with each other, which makes estimation of displacement effective. A pair of divided images which are generated from the same group image, such as $I_d\_1\_1$ and $I_d\_1\_2$, is not selected.

Here the k-th pair is denoted by R_k. One of the divided images constituting the pair R_k is denoted by $I_d\_k$, 1 and the other is denoted by $I_d\_k$, 2. These divided images $I_d\_k$, 1 and $I_d\_k$, 2 correspond to any p-th divided image $I_d\_j\_p$ generated from the j-th group image. In this embodiment, a case of selecting a pair within the shallow region or within the deep region will be described. Here a case of selecting the total K number of pairs will be described.

Possible methods that can be used for selecting the pair follow.

Selecting a pair of which area or volume of the overlapped region has at least a predetermined value (ratio).

Selecting a pair so that regions having a high number of shot images are overlapping in the divided images.

Selecting, for a divided image, a group image of which group index is within a predetermined range (e.g. group index is ±3 range) from the group image from which this divided image is generated, and selecting a divided image acquired from this group image as a pair.

Selecting divided images acquired from group images of which group indexes are continuous (group images which are temporarily continuous) as a pair.

In this embodiment, it is assumed that the displacement estimating unit 110 selects divided images of which overlapping region, with respect to each divided image, is at least 50% as a pair.

Then in step S250, the displacement estimating unit 110 estimates the displacement amount between each divided image. An example of the method of estimating the displacement amount between each divided image will be described.

First, as Expression (1) shows, the displacement estimating unit 110 acquires the similarity function F_k between the divided images $I_d\_k$, 1 and $I_d\_k$, 2 for each pair R-k (1≤k≤K) respectively.

[Math. 1]

$$F\_k(x,y,z) = f_{simil}(R\_k,x,y,z) \qquad \text{Expression (1)}$$

The similarity function F_k is a function to calculate the similarity in the case of translationally moving the relative position of the divided image $I_d\_k$, 2, which is one divided image constituting the pair R_k, with respect to the other divided image $I_d\_k$, 1 by (x, y, z).

The function $f_{simil}$ is a function that returns a higher value as the similarity between images is higher. To acquire the similarity function F_k means to acquire a function value in the case of discretely changing the translational moving amount (x, y, z), which is an argument of each function, that is, the relative positions of the images within a predetermined range. For example, to acquire the similarity function F_k means to acquire a set of (2L+1)×(2L+1)×(2L+1) number of values, which F_k returns for each case when each value of x, y and z is changed from −L to +L integer values respectively.

Furthermore, a similarity function F_k, which is closer to a continuous function, may be derived from this set using a bilinear method, a bicubic method or the like.

Based on a position obtained by translationally moving by the relative position of $I_d\_k$, 2, with respect to $I_d\_k$, 1 (i.e. the distance of the probe between the light irradiation executions), a function value determined by discretely changing the position of $I_d\_k$, 2 within a predetermined range may be acquired.

As a function to calculate the similarity, any similarity index, such as SSD, SAD, mutual information and cross-correction can be used. The similarity function may also be acquired, for example, by extracting a characteristic form from divided images, and measuring a degree of matching of the positions.

The displacement estimating unit 110 may acquire the similarity function by multiplying the result of calculating the similarity at each position shown in Expression (1) (calculating the square of the difference of each pixel value, in the case of SSD), by the partial weight images $W_d\_k$, 1 and $W_d\_k$, 2 described in step S235. By this processing, the displacement estimating unit 110 can acquire the similarity function reflecting the reliability.

In the case when the similarity cannot accurately calculate between the target divided images used in similarity calculation, this result may be discarded, and not used for subsequent processing. An example of the case when the similarity cannot be accurately calculated is the case when the similarity cannot be increased (or not changed) regardless how images are translationally moved. In this processing, the comparison result (similarity function) between divided images, which sufficiently present the same characteristics, can be selectively generated.

Then as Expression (2) shows, the displacement estimating unit 110 acquires the translational moving amount M_k of the divided image $I_d\_k$, 2 with respect to the divided image $I_d\_k$, 1, at which the function value of the similarity function F_k is at the maximum. Further, the displacement estimating unit 110 acquires the translational moving amount M_k at which the value of the similarity function F_k is at the maximum for each pair.

[Math. 2]

$$M\_k = \mathrm{argmax}\{F\_k((x,y,z)\}$$ Expression (2)

Then based on the calculated translational moving amount M_k (1≤k≤K), the displacement estimating unit 110 estimates a correction amount ΔPosI$_d$_j_p in each divided image I$_d$_j_p. The correction amount estimated here is a shift (movement) amount of the position of the object when this divided image is captured. For this calculation, an evaluation function, to maintain the translational moving amount M_k, which is an individual optimum value of the pair R_k, as much as possible, is defined. In other words, an evaluation function, of which value decreases as the position of I$_d$_k, 2 with respect to I$_d$_k, 1 deviates from the translational moving amount M_k, is defined. Expression (3) is an example of the evaluation function E_k.

[Math. 3]

$$\begin{aligned} E\_k &= (M\_k - (\Delta PosI_{d\_}k, 1 - \Delta PosI_{d\_}k, 2))^2 \\ &= (M\_k(x) - (\Delta PosI_{d\_}k, 1(x) - \Delta PosI_{d\_}k, 2(x)))^2 + \\ &\quad (M\_k(y) - (\Delta PosI_{d\_}k, 1(y) - \Delta PosI_{d\_}k, d(y)))^2 + \\ &\quad (M\_k(z) - (\Delta PosI_{d\_}k, 1(z) - \Delta PosI_{d\_}k, 2(z)))^2 \end{aligned}$$ Expression (3)

Here ΔPosI$_d$_k, 1 denotes a correction amount of the position of the divided image I$_d$_k, 1 with respect to the reference position. In the same manner ΔPosI$_d$_k, 2 denotes a correction amount of the position of the divided image I$_d$_k, 2 with respect to the reference position. When the evaluation function is defined, the similarity function F_k may be approximated to a quadratic function that fits this similarity function F_k. If the similarity function F_k can be approximated to "decreasing along the quadratic function at the periphery of the translational moving amount M_k", Expression (3) becomes a function which approximates the value of the similarity function F_k at the periphery of the translational moving amount M_k.

Based on the above mentioned evaluation function for each pair R_k (pair of I$_d$_k, 1 and I$_d$_k, 2), the displacement estimating unit 110 calculates the correction amount ΔPosI$_d$_j_p of the positions of all the divided images I$_d$_j_p with respect to the reference position, so as to minimize the cost function E, shown in Expression (4). As mentioned above, the divided images I$_d$_k, 1 and I$_d$_k, 2 correspond to any one of the divided images I$_d$_j_p.

[Math. 4]

$$E = \sum_{k=1}^{K} E\_k$$ Expression (4)

The position of the divided image with respect to the reference position after correction, when the cost function is minimized, indicates the position information of the divided image after displacement is generated by the shift of the relative positional relationship between the object and the probe.

For example, the displacement estimating unit 110 acquires a solution, to minimize the cost function E shown in Expression (4) (to make the cost function E closest to 0), by solving the linear least square method. Thereby the correction amount ΔPosI'$_d$_j_p of the position of each divided image can be uniquely calculated. In the cost function shown in Expression (4), the correction amount ΔPosI'$_d$_j_p of the position of each divided image can be uniquely determined using a linear least square method, therefore the calculation cost can be reduced.

When the pair is selected only within the shallow region or within the deep region, ΔPosI'$_d$_j_1 and ΔPosI'$_d$_j_2 may be solved separately. In other words, Expressions (1) to (4) may be separated into expressions for the shallow region and expressions for the deep region, and be solved.

In the above example, optimization of the cost function using a linear optimization method was described, but any other method may be used for optimizing the cost function. For example, the cost function may be optimized by a non-linear optimization method using repeat calculation, such as the steepest descent method and Newton's method.

In this way, the displacement estimating unit 110 acquires the position information of the divided image after displacement with respect to the reference position, by searching the correction amount of the position of each divided image so as to minimize the cost function.

The cost function may be defined to regularize the expected positional shift (movement) of the object. For example, in the case when the object is a breast, movement caused by breathing is dominant. In this case, it is expected that the movement of the object is several mm at the maximum, and the movement is temporarily continuous and smooth. Further, this movement is expected to be cyclic. Therefore regularization may be performed to prevent calculating movement, which deviated from the expected movement of the object, as mentioned above.

Furthermore, the regularization to limit the positional relationship between the regions may be performed, so that the correction amount ΔPosI$_d$_j_1 of the position in the shallow region does not deviate from the correction amount ΔPosI$_d$_j_2 of the position in the deep region. In this case, in Expressions (1) to (4), ΔPosI'$_d$_j_1 and ΔPosI'$_d$_j_2 cannot be solved separately, and must be solved together.

Any method may be used for regularization. For example, regularization can be perform by multiplying the total shift amount (moving distance) of the object in the derivation step by a predetermined weight coefficient, and adding this multiplication result to the cost function. The total of the time derivative (acceleration) of the movement of the object may be added to the cost function. Further, a value calculated based on the frequency component value of the movement of the object may be added to the cost function. Furthermore, a typical movement of the object is provided as a model, and the difference from this model may be added to the cost function as a cost.

"Minimizing the cost function" includes not only the case when the cost function becomes a strict minimum, but it also includes the case when the cost function becomes not more than a predetermined value when the candidate of the solution is changed, or the case when the change amount of the cost function becomes not more than a predetermined value. In other words, the displacement estimating unit 110 may determine that the cost function has become the minimum when the cost function satisfies a predetermined condition. Further, the user may input that the cost function has become the minimum using the operating unit 1309. In this case, the displacement estimating unit 110 determines that the cost function has becomes the minimum when an instruction is received from the operating unit 1309.

The processing in step S250 is completed by the above processing operations.

In this step, any method may be used as long as the displacement amount of each divided image, caused by the shift of relative positions between the object and the probe, can be determined.

Then in step S270, the combining unit 106 performs the processing to correct the position of each divided image by the amount of displacement estimated in step S250 (translational moving processing), and combines these corrected divided images so as to acquire an image in which displacement is corrected (hereafter "integrated image"). The combining processing to generate the integrated image is called the "second combining". The generated integrated image is outputted via the display 160.

For the region where the images overlap in the second combining, the images may be added, or only an arbitrary divided image may selected.

As described above, in the image processing system according to Embodiment 1, a group image having a higher quality than shot images is acquired, and the group image is divided to estimate the displacement amount for each depth. Thereby the displacement can be accurately estimated, and an integrated image can be generated at high precision. In other words, even if the relative positional relationship between the object and the probe is shifted while executing light irradiation, the influence thereof can be sufficiently suppressed.

Modification 1 of Embodiment 1

In Embodiment 1, a case when the probe moves while light irradiation is executed for a plurality of times was described as an example, but the above processing can be applied even for a configuration in which the prove does not move. In other words, a similar processing may be performed for an image acquired by a photoacoustic apparatus which has no function to move the probe. In this case, it is unnecessary to acquire the position information of the probe and the shot images.

Further, in this case, all the shot images and the group images overlap, and the partial images in a same region also overlap. Therefore all the partial images can be selected as pairs. Pairs may be selected based on the temporal continuity. In this case as well, image data can be acquired with suppressing the influence of body motion of the object and the like.

Modification 2 of Embodiment 1

In Embodiment 1, a case when the displacement of the object is due to translational movement was described, but the present invention can be applied in the same manner when the displacement is caused by rotational movement.

In the case of considering rotation, the displacement estimating unit 110 estimates the displacement amount and the rotational amount of each divided image in step S250, using the translational amount and the rotational amount as arguments. Then the displacement estimating unit 110 performs in step S270 the second combining after correcting each divided image based on the estimated displacement amount and the rotational amount. By this processing, an integrated image having high quality can be acquired. The translational amount and the rotational amount can be combined, or only one may be used.

If it is known in advance that displacement occurs in certain directions, only one-dimensional or two-dimensional movement may be considered. For example, if it is known that the object will unlikely move in the Z direction, then only movement on the XY plane may be used as unknown parameters. By deleting unnecessary parameters out of the unknown parameters like this, a solution can be stably determined. For example, if the object contacts the holding plate, it can be assumed that the object does not move in the direction perpendicular to the holding plate.

If it is known in advance that the characteristic of movement differs depending on the divided region, the parameter to be estimated may be changed depending on the region. For example, in the shallow region, only the translational amount may be set as an unknown parameter, and in the deep region, the translational amount and the rotational amount may be set as unknown parameters. Or in the shallow region, only the displacement amount in the XY directions may be set as an unknown parameter, and in the deep region, the displacement amount in three-dimensional directions may be set as an unknown parameter. For example, taking the constraint by the holding plate under consideration, unknown parameters used for the shallow region may be limited.

Modification 3 of Embodiment 1

In Embodiment 1, the displacement is corrected by selecting a pair within the shallow region, and a pair within the deep region. However, a pair of divided images may be generated arbitrarily.

For example, a partial image in the shallow region, acquired from a certain group image, and a partial image in the deep region acquired from another group image, may form a pair. In this case, however, $\Delta \text{PosI'}_d\_j\_1$ and $\Delta \text{PosI'}_d\_j\_2$ cannot be solved separately, but must be solved together in Expressions (1) to (4).

According to this modification, displacement can be corrected based on a higher volume of information, and an integrated image having high quality can be acquired.

Modification 4 of Embodiment 1

In step S250, the displacement amount may be estimated by converting the three-dimensional image data into two-dimensional projection image data, and using this projection image data. An example of this processing will be described.

In this modification, the displacement estimating unit 110 acquires the maximum intensity projection (MIP) data as the projection image data when the divided image $I_d\_j\_p\ (x, y, z)$ is projected in the X, Y and Z directions respectively.

The MIP data projected in the X direction is a two-dimensional spatial distribution information expressed by the Y axis and the Z axis, and is denoted by $I_{xd}\_j\_p\ (y, z)$. The MIP data projected in the Y direction is a two-dimensional spatial distribution information expressed by the Z axis and the X axis, and is denoted by $I_{yd}\_j\_p\ (z, x)$. The MIP data projected in the Z direction is a two-dimensional spatial distribution information expressed by the X axis and the Y axis, and is denoted by $I_{zd}\_j\_p\ (x, y)$.

Then the displacement estimating unit 110 acquires the similarity of the MIP data of $I_d\_k, 1$ and the MIP data of $I_d\_k$, 2, for the XY plane, the YZ plane and the ZX plane respectively. In other words, the displacement estimating unit 110 acquires the similarity as shown in the following Expressions (5) to (7).

[Math. 5]
$$FX\_k(y,z)=f_{simil}(RX\_k,y,z) \qquad \text{Expression (5)}$$

[Math. 6]
$$FY\_k(x,z)=f_{simil}(RY\_k,x,z) \qquad \text{Expression (6)}$$

[Math. 7]
$$FZ\_k(x,y)=f_{simil}(RZ\_k,x,y) \qquad \text{Expression (7)}$$

Here RX_k denotes a pair formed by two MIP data ($I_{xd}\_k$, 1 and $I_{xd}\_k$, 2) expressed by the YZ plane. In the same manner, RY_k denotes a pair formed by two MIP data ($I_{yd}\_k$, 1 and $I_{yd}\_k$, 2) expressed by the ZX plane. Also RZ_k denotes a pair formed by two MIP data ($I_{zd}\_k$, 1 and $I_{zd}\_k$, 2) expressed by the XY plane.

FX_k (y, z) is a function to calculate the similarity in the case when the relative position of one MIP data forming the RX_k pair, with respect to the other MIP data forming the RX_k pair, is translationally moved by (y, z). FY_k (x, z) is a function on the ZX plane, and FZ_k (x, y) is a function on the XY plane. For the method of calculating the similarity, the method described in step S250 can be used.

Then the displacement estimating unit 110 calculates each translational moving amount MX_k, MY_k and MZ_k (translational moving amount of $I_d\_k$, 2 with respect to $I_d\_k$, 1), for the YZ plane, the ZX plane and the XY plane respectively when the function value is at the maximum, as shown in the following Expressions (8) to (10).

[Math. 8]
$$MX\_k = (MX\_k\_y, MX\_k\_z) = \arg\max_{y,z}\{FX\_k(y, z)\} \qquad \text{Expression (8)}$$

[Math. 9]
$$MY\_k = (MY\_k\_y, MY\_k\_z) = \arg\max_{x,z}\{FY\_k(x, z)\} \qquad \text{Expression (9)}$$

[Math. 10]
$$MZ\_k = (MZ\_k\_y, MZ\_k\_z) = \arg\max_{x,y}\{FZ\_k(y, z)\} \qquad \text{Expression (10)}$$

For example, as shown in Expression (11), the average value of the components on each coordinate axis of the translational moving amount MX-k, MY_k and MZ_k is assumed to be the respective component value of the translational moving amount M_k (three-dimensional moving amount of $I_d\_k$ with respect to $I_d\_k1$) when the similarity is at the maximum.

[Math. 11]
$$M\_k = (M\_k\_x, M\_k\_y, M\_k\_z)$$
$$= \left(\frac{MY\_k\_x + MZ\_k\_x}{2}, \frac{MX\_k\_y + MZ\_k\_y}{2}, \frac{MX\_k\_z + MY\_k\_z}{2}\right) \qquad \text{Expression (11)}$$

Then using the translational moving amount M_k shown in Expression (11), the displacement estimating unit 110 estimates a position of each divided image when the cost function shown in Expression (4) is minimized, as described in step S250.

The projection direction when the three-dimensional divided image is converted into the two-dimensional projection image may be determined based on the surface shape data. The target divided images for which the projection direction is determined based on the surface shape data may only be the divided images in the shallow region, or may be all the divided images. In this case, the MIP data is acquired for the divided image $I_d\_j\_p$ (x, y, z), when projection is performed in the first direction and the second direction along the surface shape data, and the third direction, which is the normal line direction of the surface shape data respectively.

By the above processing, the displacement amount can be acquired based on the two-dimensional image data converted from the three-dimensional image data. If the three-dimensional image data is converted to the two-dimensional image data like this, calculation cost can be reduced, compared with the case of processing the three-dimensional image data directly.

In this modification, the MIP image was described as an example, but a projection method other than MIP may be used, as long as the three-dimensional image data can be converted into the two-dimensional image data. For example, the minimum intensity projection (MinIP) image may be generated instead of the MIP image.

Modification 5 of Embodiment 1

In Embodiment 1, each group image is divided into two, the shallow region and the deep region, in accordance with the distance from the surface of the object. However, three or more regions may be generated by division. For example, the region may be further divided into at least two in the X axis direction or in the Y axis direction in FIG. 9. Also for example, a partial image corresponding to the shallow region may be further divided, or a partial image corresponding to the deep region may be further divided. Thereby displacement at a higher order can be handled.

Embodiment 2

In Embodiment 1, a plurality of group images are divided into a plurality of divided images respectively in accordance with the distance from the surface of the object. In Embodiment 2, however, the dividing surfaces are determined based on an image (hereafter "second image") acquired by imaging the object using a modality other than a photoacoustic apparatus.

In Embodiment 2, an image acquired by performing ultrasonic echo imaging on the object (three-dimensional ultrasonic image, hereafter "echo image") is used as the second image. The unit to perform the ultrasonic echo imaging may be integrated in the photoacoustic apparatus that captures shot images.

The functional configuration of the image processing apparatus according to Embodiment 2 is the same as in FIG. 1. However the data held by the data server 150 and the content of the processing operations performed by the acquiring unit 102 and the dividing unit 108 are different from Embodiment 1.

In Embodiment 2, the data server 150 holds an echo image of the object in addition to a series of shot image, the surface shape data and the distance data.

The acquiring unit 102 acquires the echo image of the object, in addition to the shot images, the surface shape data and the distance data, from the data server 150.

The dividing unit 108 divides each group image into a plurality of divided images respectively, based on the acquired echo image.

Figure 5:
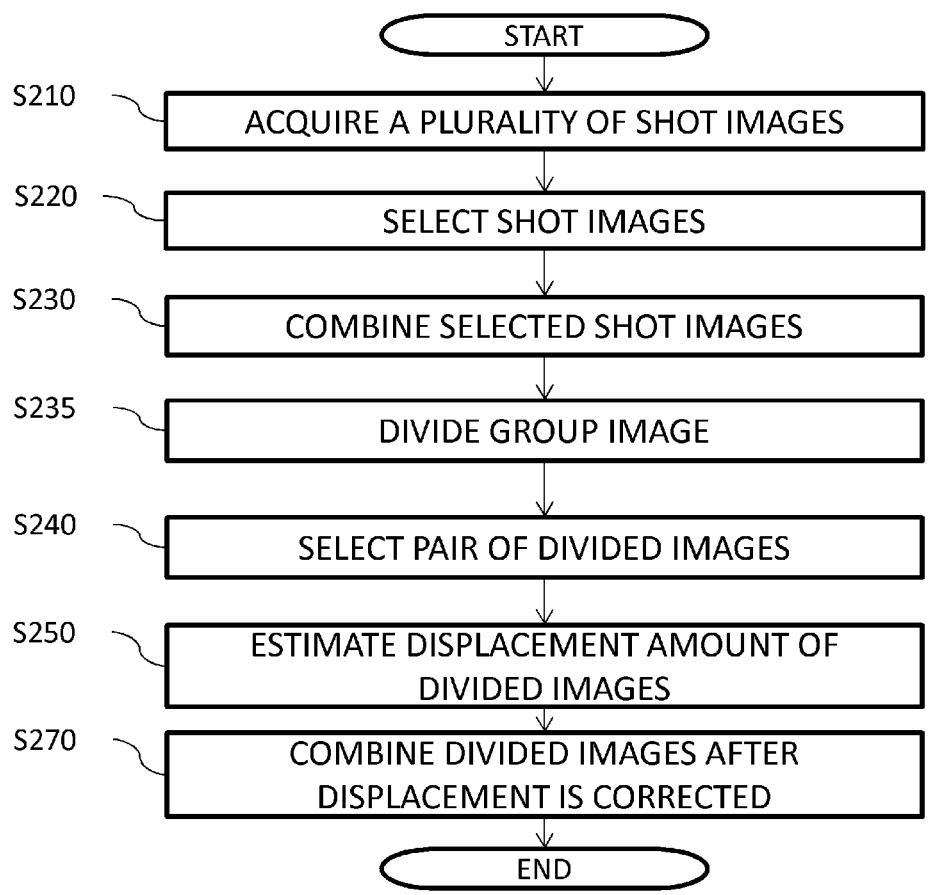
FIG. 5 is a flow chart depicting a processing procedure of the image processing apparatus according to Embodiment 1.
Figure 10:
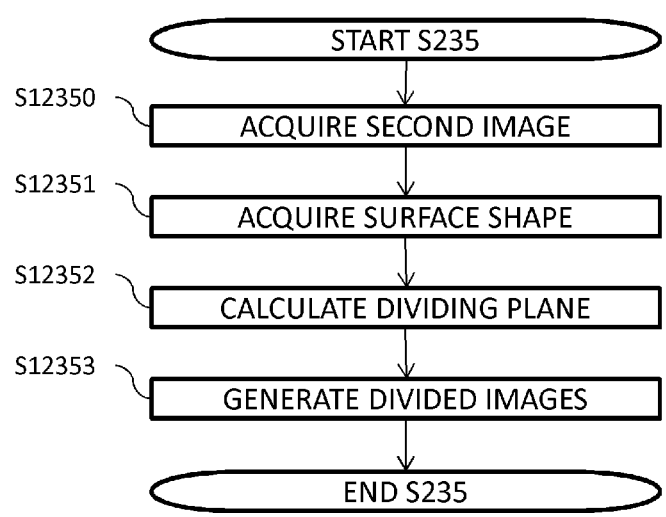
FIG. 10 is a flow chart depicting an image dividing processing according to Embodiment 2.

The flow chart of the processing operations performed by the image processing apparatus 100 according to Embodiment 2 is the same as FIG. 5, except for a part of the processing in step S235. FIG. 10 is a flow chart depicting an example of the processing according to Embodiment 2.

First in step S12350, the acquiring unit 102 acquires the second image stored in the data server 150.

Then in step S12351, the acquiring unit 102 acquires the surface shape data of the object stored in the data server 150. If the surface shape of the object can be acquired from the echo image by a known image processing method, this step may be omitted.

Then in step S12352, the dividing unit 108 divides a plurality of group images into a plurality of divided images based on the second image. In concrete terms, the subcutaneous fat layer and the mammary gland layer are extracted from the echo image using a known image analyzing method, and calculates a curved surface indicating the boundary of these layers as the dividing surface. The chest wall may also be extracted, and a curved surface indicating the boundary of the mammary gland layer and the chest wall may be calculated as another dividing surface.

The processing in step S12353 is the same as the above described processing in step S2353, hence detailed description is omitted.

According to Embodiment 2, the divided images divided at a more appropriate dividing plane can be generated, and displacement amount of the divided images can be accurately estimated.

In Embodiment 2, the subcutaneous fat layer and the mammary gland layer are extracted based on the echo image, and the boundary thereof is set as the dividing plane, but the dividing plane may be set by a different method. For example, blood vessels are extracted from the echo image, the extracted blood vessels are classified into superficial blood vessels and deep blood vessels using a known mechanical learning method, and a boundary thereof is set as a dividing surface. Or a region where a tumor exists (tumor region) is extracted from the echo image, and the image is classified into a layer of which depth from the surface of the object is shallower than the tumor region, a layer which is deeper than the tumor region, and a layer at a depth including the tumor region, and the boundaries thereof are set as the dividing planes.

Other Embodiments

The description of each embodiment is an example to described the present invention, and the present invention may be carried out by appropriately changing or combining each embodiment without departing from the essential content of the invention.

For example, the present invention may be carried out as an image processing apparatus that executes at least a part of the above mentioned processing operations. The present invention may be carried out as an image processing method that includes at least a part of the above processing operations. The above processing operations and units may be freely combined as long as no technical inconsistency is generated.

The present invention may be carried out as a part of an object information acquiring apparatus, including a signal acquiring unit that acquires a signal obtained by converting an acoustic wave generated from the object by an acoustic element, and an information acquiring unit that generates an object image by performing an operation for the acquired signal.

In the description of the embodiments, processing is performed for a series of shot images captured by the photoacoustic apparatus, but the applicable range of the present invention is not limited to this, and the present invention can be applied to various apparatuses which register a plurality of image data.

For example, the above mentioned processing may be performed on a plurality of images acquired by an ultrasonic diagnostic apparatus which acquires image data by an ultrasonic echo. Further, the above mentioned processing may be performed on a plurality of images acquired by a diffuse optical tomography (DOT) apparatus, an optical coherence tomography (OCT) apparatus or the like. Furthermore, the above mentioned processing may be performed on a plurality of images acquired using X-rays, such as an X-ray fluoroscopic image acquiring apparatus and an X-ray tomographic image acquiring apparatus.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2017-001263, filed on Jan. 6, 2017, which is hereby incorporated by reference herein in its entirety.

What is claimed is:

1. An image processing apparatus, comprising:
   an image acquiring unit that acquires a plurality of object images captured by imaging an object for a plurality of times;
   a shape acquiring unit that acquires shape information, which is information representing a shape of the object;
   an image dividing unit that divides each of the plurality of object images into at least two partial images, based on the shape information; and
   an image registering unit that registers the divided partial images to each other,
   wherein the image acquiring unit comprises (a) a signal acquiring unit that acquires a signal obtained by converting by an acoustic element an acoustic wave generated in an object by irradiating the object with light, and (b) an information acquiring unit that generates the object image by performing an operation on the acquired signal.

2. The image processing apparatus according to claim 1, further comprising an image generating unit that generates an integrated image by combining the registered partial images.

3. The image processing apparatus according to claim 1, wherein the image dividing unit divides each of the plurality of object images into at least a first partial image corresponding a shallow region, which is a region near a surface of the object, and a second partial image corresponding to a deep region, which is a region located more distant from the surface of the object than with the shallow region.

4. The image processing apparatus according to claim 3, wherein
   the shape information is information representing the surface shape of the object, and
   the image dividing unit divides each of the plurality of object images, based on the distance from the surface of the object.

5. The image processing apparatus according to claim 3, wherein the image dividing unit divides each of the plurality of object images, based on the clinical information on the object.

6. The image processing apparatus according to claim 3, wherein the image dividing unit divides each of the plurality of object images, based on the information acquired by analyzing the object image.

7. The image processing apparatus according to claim 3, wherein
   the image acquiring unit acquires a second object image captured by imaging the object by using a modality that is different from modality used for acquiring the object image, and
   the image dividing unit divides each of the plurality of object images, based on the information acquired by analyzing the second object image.

8. The image processing apparatus according to claim 3, wherein the image registering unit registers the first partial images, and registers the second partial images.

9. The image processing apparatus according to claim 1, wherein
   each of the partial images is a three-dimensional image, and
   the image registering unit generates a two-dimensional projection image from the partial image, and registers the generated projection image.

10. The image processing apparatus according to claim 1, wherein the image registering unit registers partial images generated by dividing different object images.

11. The image processing apparatus according to claim 1, wherein the object is a human body, and the image dividing unit deletes from the partial images information on a region corresponding to outside the body.

12. An image processing method, comprising:
   acquiring a plurality of object images captured by imaging an object for a plurality of times;
   acquiring shape information, which is information to represent a shape of the object;
   dividing each of the plurality of object images into at least two partial images, based on the shape information; and
   registering the divided partial images to each other,
   wherein the acquiring the plurality of object images comprises (a) acquiring a signal obtained by converting by an acoustic element an acoustic wave generated in an object by irradiating the object with light, and (b) generating the object image by performing an operation on the acquired signal.

13. A non-transitory computer-readable storing medium recording a computer program for causing a computer to perform a method comprising the steps of
   acquiring a plurality of object images captured by imaging an object for a plurality of times;
   acquiring shape information, which is information to represent a shape of the object;
   dividing each of the plurality of object images into at least two partial images, based on the shape information; and
   registering the divided partial images to each other,
   wherein the acquiring the plurality of object images comprises (a) acquiring a signal obtained by converting by an acoustic element an acoustic wave generated in an object by irradiating the object with light, and (b) generating the object image by performing an operation on the acquired signal.

* * * * *